United States Patent [19]

Gillis

[11] Patent Number: 4,483,339

[45] Date of Patent: Nov. 20, 1984

[54] VASCULAR SURGERY ROLL

[76] Inventor: Rolando Gillis, 10721 S.W. 49th Terrace, Miami, Fla. 33165

[21] Appl. No.: 584,765

[22] Filed: Feb. 29, 1984

Related U.S. Application Data

[63] Continuation of Ser. No. 343,864, Jan. 29, 1982, abandoned.

[51] Int. Cl.³ .............................................. A61B 17/04
[52] U.S. Cl. .................................... 128/334 R; 3/1.4
[58] Field of Search ............... 128/1 R, 334 R, 334 C, 128/335; 3/1, 1.4

[56] References Cited

U.S. PATENT DOCUMENTS

| | | | |
|---|---|---|---|
| 3,562,820 | 2/1971 | Braun | 3/1.4 |
| 3,710,777 | 1/1973 | Sparks | 3/1 |
| 3,938,524 | 2/1976 | Sparks et al. | 3/1.4 |
| 3,993,078 | 11/1976 | Bergentz et al. | 128/334 R |
| 4,182,339 | 1/1980 | Hardy, Jr. | 128/334 R |
| 4,190,909 | 3/1980 | Ablaza | 128/334 R |
| 4,267,842 | 5/1981 | Archibald | 128/334 R |

FOREIGN PATENT DOCUMENTS

WO80/02641 12/1980 PCT Int'l Appl. ...................... 3/1.4

Primary Examiner—C. Fred Rosenbaum
Assistant Examiner—Michelle N. Lester
Attorney, Agent, or Firm—John C. Malloy

[57] ABSTRACT

For use in vascular surgery a roll of wound strand having an outer predetermined size diameter corresponding to the inside diameter of an opened blood conduit into which it is temporarily inserted with a pigtail of one end of the roll of strand extending from the blood conduit to be used to pull the strand from the roll until the roll is completely removed from the blood conduit after it has been stitched together.

3 Claims, 5 Drawing Figures

VASCULAR SURGERY ROLL

This is a continuation of application Ser. No. 343,864 filed Jan. 29, 1982, now abandoned.

BACKGROUND OF THE INVENTION

Oftentimes a surgeon is required to open a blood conduit, such as a vein or artery, for the purpose of removing plaque or for repairing a damaged blood conduit. Sometimes a slit is made longitudinally and sometimes it is a cross-cut, while at other times it may be a damaged conduit, such as might occur during an accident. In any event, it is difficult at times to sew the blood conduit back together again. This invention is of a vascular surgery roll which may be positioned within the conduit at the zone which is to be sewn together and, after it is sewn together, it is removed by pulling it through a slight opening in the vein or artery so that it unwinds gradually, the pigtail being outside of the vein or artery once it is sewn up, as is explained more fully hereinafter.

DESCRIPTION OF THE PREFERRED EMBODIMENTS

Figure 1:
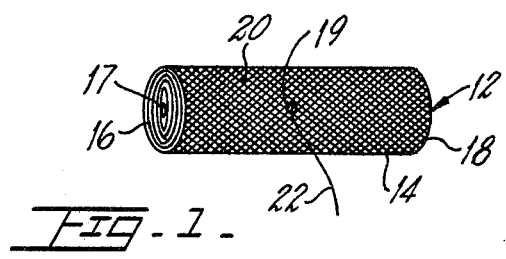
FIG. 1 is a perspective view of a vascular surgery roll in a first embodiment.
Figure 2:
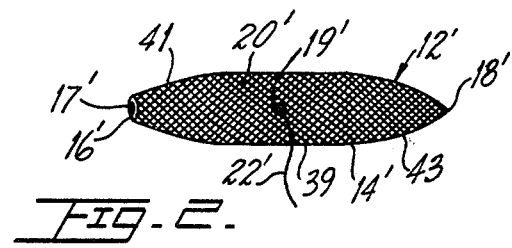
FIG. 2 is an alternative embodiment of the roll shown in FIG. 1.

Referring to the drawings wherein like reference characters designate like or corresponding parts throughout the several views and referring particularly to FIG. 1, the numeral 12 designates the roll which has an outside surface 14, a first end 16, a second end 18, and is composed of windings wherein the convolutions, such as that designated by the numeral 20 are not strictly circumferential but somewhat elliptical in that they extend in a slantwise direction rather than completely around the device. The roll also has a hole 17 in the end face which extends through it and a small hole 19 from which a pigtail 22 extends. The device shown in FIG. 2 is quite similar to that shown in FIG. 1 with the exception that the ends are tapered so that there is provided a flat zone 39 and tapered end zones 41 and 43 which converge to the ends 16' and 18'. The other portions of FIG. 2 which correspond to FIG. 1 are designated with numerals corresponding to those in FIG. 1 with the prime designation applied and are not here further described in order to shorten this application.

Figure 3:
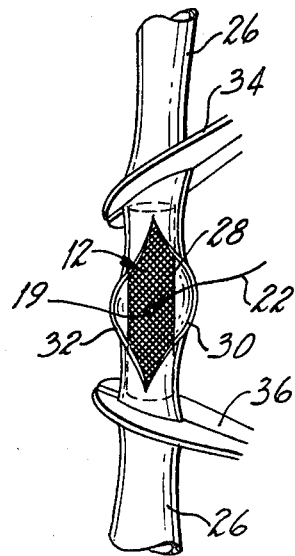
FIG. 3 is a view in detail illustrating the positionment of the roll in a section of a vein or artery that has been isolated by clamp means.
Figure 4:
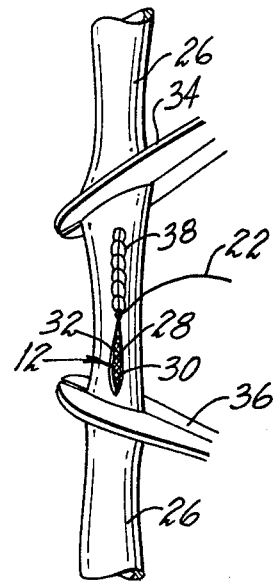
FIG. 4 is a view similar to FIG. 3 and illustrates the vein or artery partially closed.

Referring to FIG. 3, the roll is used as follows:

Once the vein or artery has been isolated as by the clamps 34 and 36, an opening 28 with side edges 30 and 32 is to be sewn together. In order to do this the roll 12 is inserted into the isolated section with the pigtail 22 extending from the opening. Thereafter, it is sewn together as indicated by the numeral 38 with the pigtail extending through the slit opening. Thereafter, the pigtail is withdrawn as the roll unwinds to the point where it no longer exists.

Figure 5:
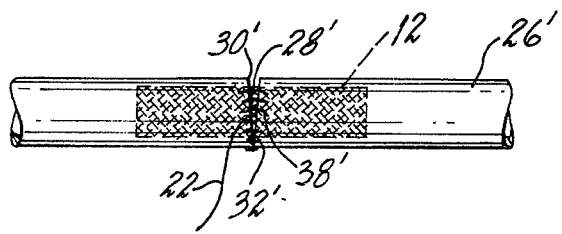
FIG. 5 is a view similar to FIGS. 3 and 4 with the difference that there is illustrated a blood conduit which is in abutting engagement with one another and is to be circumferentially sewn together about the roll.

In FIG. 5, the ends 28' and 30' are of a vein or artery 26' and the roll 8 is inserted and the pigtail 22 extends through the opening between the abutting ends so that when it is sewn together as indicated by the numeral 38', the pigtail may be utilized to withdraw the wound line removing the roll entirely.

It will be seen that this provides a plug at the site where the vein or artery is to be sewn together which greatly facilitates the ability of the surgeon to perform the stitching operations. There is no rejection problem of the foreign article within the body because it is completely removed.

Each convolution in a preferred embodiment is a monofilament or it may be a twisted group of fine filaments defining a strand of filaments and for purposes of this description the same may be regarded as a strand in either embodiment.

While the instant invention has been shown and described herein in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus and articles.

What is claimed is:

1. A blood vessel support structure designed to support portions of opened blood vessels surrounding an opening therein during closing of the opening, said support structure comprising, a roll formed from a length of strand wound upon itself to form windings, said windings collectively defining the configuration of said roll to include:

(a) an outer surface dimensioned and disposed for contronting, substantially supporting engagement with an inner surface of the blood vessel in which it is positioned, (b) a first end and a second end each integrally formed at respective opposite ends of said outer surface, (c) a centrally disposed channel extending coaxially through said roll and along the length thereof between said first and said second ends, said channel disposed and structured to allow blood flow therethrough and defining a substantially cylindrical inner surface spaced inwardly a predetermined distance from said outer surface along at least a major portion of the length thereof, (d) said windings successively extending from said outer surface to said inner surface to define a continuous cylindrical wall having a thickness equal to said predetermined distance between said outer surface and said inner surface, said predetermined distance dimensioned to be determinative of the amount of support presented to the blood conduit;

a pigtail defined by a distal extremity of said length of strand and disposed to extend from said inner surface through an aperture means formed in said wall outwardly therefrom a sufficient distance to protrude through the opening of the blood vessel, whereby tension applied exteriorly of the blood vessel to said pigtail will cause said strand to be unwound along its length and a successive removal of said windings from said inner surface to said outer surface and removal of said roll from the blood vessel.

2. A structure as in claim 1 wherein each of said first end and said second ends comprises a tapered zone extending substantially from said outer surface to said inner surface.

3. A structure as in claim 1 wherein said aperture formed in said wall through which said pigtail extends is disposed intermediate said first and said second ends of said roll and disposed substantially transverse to the longitudinal axis thereof.

* * * * *